United States Patent [19]

DeLuca et al.

[11] 4,313,942

[45] Feb. 2, 1982

[54] ACTIVATED VITAMIN D RODENTICIDES

[75] Inventors: Hector F. DeLuca; Heinrich K. Schnoes, both of Madison; Herbert E. Paaren, Verona; Helen Frank, Madison, all of Wis.

[73] Assignee: Wisconsin Alumni Research Foundation, Madison, Wis.

[21] Appl. No.: 83,023

[22] Filed: Oct. 9, 1979

[51] Int. Cl.³ .............................................. A61K 31/59
[52] U.S. Cl. .................................. 424/236; 260/397.2
[58] Field of Search ...................... 424/236; 260/397.2

[56] References Cited

U.S. PATENT DOCUMENTS 4,035,493 7/1977 DeLuca et al. ...................... 424/236
4,226,788 10/1980 DeLuca et al. .................. 260/397.2

OTHER PUBLICATIONS

"Steroids" (1977) vol. 30, No. 2, Article by Pelc et al., pp. 193–201.

Primary Examiner—Elbert L. Roberts
Attorney, Agent, or Firm—Howard W. Bremer

[57] ABSTRACT

The invention provides a method for chemically activating vitamin D compounds to obtain active rodenticidal preparations.

The activated vitamin D preparation offers an effective and relatively inexpensive rodenticidal material.

11 Claims, No Drawings

ACTIVATED VITAMIN D RODENTICIDES

The invention described herein was made in the course of work under a grant or award from the Department of Health and Human Services.

TECHNICAL FIELD

This invention relates to the preparation of novel rodenticides.

More specifically this invention relates to a process whereby vitamin D compounds are chemically activated to yield preparations exhibiting high rodenticidal activity.

BACKGROUND ART

The D-vitamins (i.e., vitamin $D_3$ and vitamin $D_2$) are well-known for their regulatory effect on calcium and phosphorus metabolism. In the normal animal these compounds promote intestinal calcium transport and raise blood calcium and phosphorus levels. Presumably because of their regulatory function in mineral metabolism, the D-vitamins, when administered in superphysiological doses can be highly toxic to the animal. This toxic effect is well-known and has been exploited for some time through the use of vitamin $D_3$ or $D_2$ as rodenticidal agents. However, rodenticidal applications of vitamin $D_3$ and $D_2$ require relatively large amounts of these compounds which often lead to bait-shyness or bait refusal by the rodent and hence reduce the effectiveness of these compounds in rodent control, while at the same time aggravating the problems associated with secondary poisoning.

To avoid these problems the use of vitamin D analogs, e.g., $1\alpha$-hydroxyvitamin $D_3$, $1\alpha$-hydroxyvitamin $D_2$ and 1,25-dihydroxyvitamin $D_3$, compounds showing much higher rodenticidal activity than $D_3$ itself, have been proposed (U.S. Pat. No. 4,035,493). However, the relatively high cost of preparation of these compounds in pure form may, as a practical matter, limit their application in the field.

DISCLOSURE OF INVENTION

It has now been found that a highly potent rodenticide can be obtained from readily available and inexpensive vitamin D compounds (e.g., vitamins $D_3$ and $D_2$) by a technically simple chemical activation process. This process involves a series of chemical reaction steps which, applied for example to vitamin $D_3$ or vitamin $D_2$, yield a rodenticidal preparation of a potency very significantly greater than that of the starting materials. This chemical activation can be accomplished in good yields and does not require purification of intermediates and is therefore simple in practice and economical in cost and effort.

BEST MODE FOR CARRYING OUT THE INVENTION

This activation process involves several chemical reaction steps which may be summarized as follows:

(1) Treatment of a vitamin D compound with an alkyl- or phenylsulfonyl halide (e.g., toluenesulfonylchloride, or methanesulfonylchloride) in pyridine solution, followed by, (2) alcoholysis of the product resulting from step (1) in a solution of a low molecular-weight alcohol (e.g., methanol, ethanol, isopropanol) containing a suitable buffer (e.g., $NaHCO_3$, NaOAc), followed by, (3) allylic oxidation of the product resulting from step (2) in a halocarbon solvent (e.g., methylene chloride, chloroform) preferably containing hydrogen peroxide or an alkylhydroperoxide (e.g., t-butylhydroperoxide) utilizing selenium dioxide as the oxidant, followed by (4) treatment of the product resulting from step (3) with an organic carboxylic acid (e.g., formic acid, acetic acid, halo acetic acids), and finally, (5) treatment of the product from step (4) with dilute base (e.g., 0.1–0.5 M methanolic KOH) or, alternatively, treatment of the product resulting from step (4) with a hydride reducing agent (e.g., $LiAlH_4$).

The product obtained after step (5) is the active rodenticide preparation. This product may be used as such as rodenticide, or, if desired, it may be purified further by chromatography and subsequent crystallization using conventional methods.

Although this activation process may be applied to vitamin D compounds such as vitamin $D_3$ and $D_2$ as well as their known side chain hydroxylated forms, including 25-hydroxyvitamin $D_3$, the preferred substrates for activation are vitamin $D_3$ and vitamin $D_2$.

The production and rodenticidal activity of these activated vitamin D preparations of this invention are further illustrated by the following examples:

EXAMPLE 1

Activation of Vitamin $D_3$ 750 mg of p-toluenesulfonyl chloride is added to 500 mg of vitamin $D_3$ in 1.5 ml of dry pyridine and the solution is stirred for 30 hr at 5° C. At the end of this time the reaction mixture is poured over ice-saturated $NaHCO_3$ solution and stirred for 0.5 hr. The aqueous solution is extracted with 4×30 ml portions of $Et_2O$. The organic extract is wshed with a 1×50 ml portion of saturated $NaHCO_3$, 2×50 ml portions of 3% HCl, 1×50 ml portion of saturated NaCl, dried over $MgSO_4$ and the solvent removed in vacuo.

The crude material obtained from the previous reaction is taken up in a minimum amount of dry benzene and added to a solution of 1.5 g of $NaHCO_3$ in 10 ml of anhydrous methanol. This mixture is then heated to 60° C. for 18 hr with constant stirring. At the end of this time the reaction is transferred into a separatory funnel, diluted with 80 ml of $Et_2O$ and washed twice with $H_2O$. The organic layer is then dried over $MgSO_4$ and the solvent is removed in vacuo.

To a stirring solution of 20 ml of $CH_2Cl_2$ is added 63 mg of $SeO_2$ and 315 $\mu$l of t-BuOOH (bp 34° at 25 mm). After 30 min the reaction mixture is diluted with $CH_2Cl_2$ to a volume of 50 ml and cooled to 10°–15° and product from the previous reaction is added to the oxidizing solution in a small amount of $CH_2Cl_2$. After 45 min the reaction is quenched by the addition of 20 ml of 10% NaOH. This solution is transferred to a separatory funnel and diluted with 250 ml of $Et_2O$. The organic layer is washed with 3×50 ml portions of 10% NaOH, 1×100 ml portion of $H_2O$, dried over $MgSO_4$ and the solvent removed in vacuo.

The material obtained from the preceding reaction is taken up in 10 ml of glacial acetic acid and heated to 55° for 15 min. The cooled reaction mixture is then added dropwise to a stirring solution of ice/$NaHCO_3$. When completely neutralized the aqueous solution is extracted with 3×50 ml of Et₂O. The organic extract is washed once with water and dried over MgSO₄. This ether solution is then treated with 100 mg of LiAlH₄ for 1.0 hr at room temperature. Careful quenching with 5% NaOH solution followed by drying of the ether phase with MgSO₄ and removal of the solvent in vacuo yields 230 mg of the active rodenticide, as an oil. If the rodenticide is to be obtained in crystalline form, the oil obtained as above is passed through a silica gel column (1×30 cm) eluted with 60% ethylacetate:hexane and the eluted material is then crystallized from pentane:ethyl ether solutions.

EXAMPLE 2

The rodenticide prepared as described in Example 1 (not crystallized) was dissolved in cottonseed-soybean oil (100 mg/5 ml oil). It was added at a level of 100 mg/kg diet carefully mixed to homogeneity. The diet was a complete semisynthetic diet of Suda et al. (*J. Nutrution* 100, 1049–1052, 1972). Vitamin $D_3$ at the same level (100 mg/Kg) was incorporated into an identical amount of the same diet at the same level (100 mg/kg).

Normal, mature male rats (300–350 g body weight) were divided into two groups of 6 animals each. Group I rats received the diet containing vitamin $D_3$ and Group II received the diet containing vitamin $D_3$ activated by the process of Example I. Food consumption and survival was recorded. Results are tabulated below. The data clearly show that rats receiving vitamin $D_3$ were not affected, while all rats consuming the diet containing activated vitamin $D_3$ died by the fifth day. The dead animals showed hemorrhagic and calcified kidneys and other organs, symptoms characteristic of severe vitamin D intoxication. As much as 2.2 g per kg of diet is required before ordinary vitamin $D_3$ has the same toxic effect as the activated vitamin D. The activation therefore reduces the amount of vitamin D required by a factor of at least 22.

| GROUP I | | | | | | |
| --- | --- | --- | --- | --- | --- | --- |
| 6 Albino Rats | Diet consumed/day | | | | | # killed/total |
| Holtzman Company | 1 | 2 | 3 | 4 | 5 | |
| Average wt: 320 g | 15g | 15g | 15g | 15g | 15g | 0/6 (5 days) |
| Diet: 100 μg vitamin D₃/gram of diet | | | | | | |
| GROUP II | | | | | | |
| 6 Albino Rats | 1 | 2 | 3 | 4 | 5 | # killed/total |
| Holtzman Company | 15g | 8g | 2g | — | — | 6/6 (5 days) |
| Diet: 100 μg activated vitamin D₃/gram of diet | | | | | | |

EXAMPLE 3

Activation of Vitamin $D_2$

Vitamin $D_2$ (500 mg), is subjected to the chemical activation process, involving tosylation, followed by methanolysis in NaHCO₃/MeOH, subsequent oxidation with ScO₂/t-butyl-hydroperoxide, followed by treatment with glacial acetic acid, exactly as described in Example 1. The resulting product is then subjected to treatment with 0.1 M KOH in methanol (50° 2 hr) to obtain 200 mg of the active rodenticide preparation, which is similar in potency to the preparation described in Example 1.

After chromatography (silica gel column) eluted with 60% ethyl acetate in hexane, the material may be crystallized from pentane/ether to obtain a crystalline rodenticide preparation.

The present invention thus provides a highly effective rodenticide preparation. The rodenticide is readily and economically prepared in a five-step sequence which does not require purification of intermediates. The preparation of this rodenticide in about 50% yield from vitamin D combined with its much higher rodenticidal activity (i.e., at least 20–30 times more potent than vitamin $D_3$) make it a preferred agent for rodent control. The preparation should be particularly effective for the control of rats resistant to commercial rodenticides (e.g., warfarin) and is also advantageously used for the control of other rodents (e.g., mice) or other vertebrate pests (e.g., birds). The high potency of the material combined with its delayed onset of action should overcome problems of bait-avoidance or taste rejection encountered with previously known rodenticides.

In addition to the foregoing advantage the rodenticides of the present invention appear to be tasteless to the rodent and hence will not engender "bait-shyness" in the animals. Furthermore, the rodenticidal preparations of this invention will be metabolized quite rapidly within the animal body—usually within 48 hours after a small dose. Thus, rodents ingesting the rodenticides of this invention will not retain this material in their bodies and should therefore present no secondary poisoning danger to those animals consuming such rodents. This is, of course, in contrast with the use of calciferol or cholecalciferol, where ingestion of much larger quantities are required for kill, and where retention of the ingested material in unaltered form in the rodent can present a real secondary poisoning hazard.

Although there is no intention to be bound by theoretical considerations, it is believed that the rodenticides of this invention function by superstimulating calcification mechanism in the rodent and are then degraded within the rodent body while calcification continues at a high rate.

We claim:

1. A process for improving the rodenticidal efficacy of vitamin D compounds which comprises:
   (1) treating vitamin D compounds with an alkyl- or phenylsulfonyl halide whereby a product comprising the 3-sulfonyl derivatives of the vitamin D-compound is obtained;
   (2) subjecting the product from step (1) to alcoholysis under buffered conditions in a low molecular weight alcohol whereby a product comprising the corresponding cyclovitamin D is obtained;
   (3) allylically oxidizing the product obtained in step (2), utilizing SeO₂ as the oxidizing agent, whereby a product comprising the 1α-hydroxylated cyclovitamin D is obtained;
   (4) treating the product obtained in step (3) with a low molecular weight organic carboxylic acid to obtain a product comprising the corresponding 1α-hydroxy-3-0-acyl vitamin D compound;
   (5) treating the product obtained in step (4) with a dilute alcoholic base whereby a product comprising the corresponding 1α-hydroxy vitamin D compounds is obtained; and
   (6) recovering the product of step (5).

2. The process of claim 1 wherein the starting vitamin D compounds subjected to treatment have the general structure

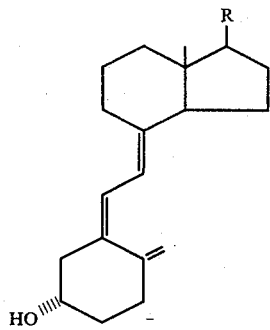

where R is a steroid side chain selected from the following configurations,

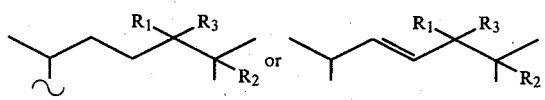

wherein each of $R_1$ and $R_2$ is selected from hydrogen, hydroxy, and 0-acyl and where $R_3$ is hydrogen or lower alkyl.

3. The process of claim 2 wherein the starting material is vitamin $D_3$.

4. The process of claim 2 wherein the starting material is vitamin $D_2$.

5. The process of claim 1 wherein the product of step (4) is treated with a hydride reducing agent whereby a product comprising the corresponding $1\alpha$-hydroxy vitamin D compound is obtained, and recovering the said product.

6. The process of claim 5 wherein the hydride reducing agent is $LiAlH_4$.

7. The process of claims 1 or 5 wherein the sulfonyl halide is $\pi$-toluenesulfonylchloride or methanesulfonylchloride.

8. The process of claims 1 or 5 wherein the alcoholysis is carried out in a methanol or ethanol solvent containing $NaHCO_3$ or NaOAc as a buffer.

9. The process of claims 1 or 5 wherein the selenium dioxide oxidation is carried out in the presence of an alkylhydroperoxide.

10. The process of claims 1 or 5 wherein the organic acid used is formic or acetic acid.

11. The process of claims 1 or 5 wherein the product from step (5) is obtained in crystalline form by conventional chromatographic and crystallization procedures.

* * * * *